US007540870B2

(12) United States Patent
Babaev (10) Patent No.: US 7,540,870 B2
(45) Date of Patent: Jun. 2, 2009

(54) ABLATIVE ULTRASONIC-CRYOGENIC APPARATUS

(75) Inventor: Eilaz Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 171 days.

(21) Appl. No.: 11/845,220

(22) Filed: Aug. 27, 2007

(65) Prior Publication Data
US 2008/0039745 A1 Feb. 14, 2008

Related U.S. Application Data

(63) Continuation-in-part of application No. 11/463,187, filed on Aug. 8, 2006, now abandoned.

(51) Int. Cl.
*A61B 18/18* (2006.01)
*A61B 18/04* (2006.01)

(52) U.S. Cl. .............. 606/20; 601/2; 601/3; 606/27; 606/28; 606/41; 606/169; 606/171

(58) Field of Classification Search .............. 600/439; 601/2, 3; 604/22; 606/20–23, 27, 28, 41, 606/169–171
See application file for complete search history.

(56) References Cited

U.S. PATENT DOCUMENTS

| 3,220,414 A | 11/1965 | Johnston |
| 3,237,623 A | 3/1966 | Gordon |
| 3,589,363 A | 6/1971 | Banko et al. |
| 3,823,717 A | 7/1974 | Pohlman et al. |
| 3,889,680 A | 6/1975 | Armao |
| 4,015,606 A | 4/1977 | Mitchiner et al. |
| 4,082,096 A | 4/1978 | Benson |
| 4,202,336 A * | 5/1980 | van Gerven ............... 606/21 |
| 4,528,979 A | 7/1985 | Marchenko et al. |
| 4,582,181 A | 4/1986 | Samson |
| 4,749,376 A * | 6/1988 | Kensey et al. ............... 604/22 |
| 4,823,790 A | 4/1989 | Alperovich et al. |
| 4,832,022 A | 5/1989 | Tjulkov et al. |
| 4,946,460 A | 8/1990 | Merry et al. |
| 4,960,134 A | 10/1990 | Webster, Jr. |
| 5,076,276 A | 12/1991 | Sakurai et al. |
| 5,078,713 A | 1/1992 | Varney |

(Continued)

OTHER PUBLICATIONS

Valentin Fuster, MD, PhD, FACC, et al., ACC/AHA/ESC Guidelines for the Management of Patients with Atrial Fibrillation: A Report of the American College of Cardiology/American Heart Association Task Force on Practice Guidelines and the European Society of Cardiology Committee for Practice Guidelines and Policy Conferences, J Am Coll Cardiol 2001; vol. 38: No. 4, 1266i-1xx, Harcourt Publishers Ltd, London, England. See 1266xxxvi-1266l.

(Continued)

*Primary Examiner*—Michael Peffley
*Assistant Examiner*—Vincent Sica (57) ABSTRACT

An ablative apparatus that can be used to treat atrial fibrillation and other cardiac arrhythmias by ablating cardiac tissue is disclosed. When the distal end of the apparatus reaches the tissue to be ablated, an ablation probe driven by a transducer is vibrated. Scratching the tissue with abrasive members, the vibrating ablation probe is capable of mechanically ablating tissues. This mechanical ablation may be utilized to penetrate epicardial fat, thereby exposing the underlying myocardium. The ablative apparatus may then be used subject the exposed myocardium to mechanical ablation, cryoablation, ultrasonic ablation, and/or any combination thereof.

13 Claims, 6 Drawing Sheets

U.S. PATENT DOCUMENTS

| | | | |
|---|---|---|---|
| 5,108,390 A | 4/1992 | Potocky | |
| 5,139,496 A | 8/1992 | Hed | |
| 5,211,646 A * | 5/1993 | Alperovich et al. | 606/23 |
| 5,281,215 A | 1/1994 | Milder | |
| 5,295,484 A | 3/1994 | Marcus et al. | |
| 5,334,181 A | 8/1994 | Rubinsky et al. | |
| 5,423,807 A | 6/1995 | Milder | |
| 5,433,717 A | 7/1995 | Rubinsky et al. | |
| 5,452,582 A | 9/1995 | Longsworth | |
| 5,474,531 A | 12/1995 | Carter | |
| 5,520,682 A | 5/1996 | Baust et al. | |
| 5,611,807 A | 3/1997 | O'Boyle | |
| 5,649,936 A | 7/1997 | Real | |
| 5,672,172 A * | 9/1997 | Zupkas | 606/20 |
| 5,716,353 A | 2/1998 | Matsuura | |
| 5,728,062 A * | 3/1998 | Brisken | 604/22 |
| 5,735,811 A * | 4/1998 | Brisken | 604/22 |
| 5,792,140 A | 8/1998 | Tu et al. | |
| 5,807,307 A * | 9/1998 | Parisi et al. | 604/22 |
| 5,807,391 A | 9/1998 | Wijkamp | |
| 5,824,005 A | 10/1998 | Motamedi et al. | |
| 5,843,152 A | 12/1998 | Tu et al. | |
| 5,876,399 A | 3/1999 | Chia et al. | |
| 5,899,898 A | 5/1999 | Arless et al. | |
| 5,899,899 A | 5/1999 | Arless | |
| 5,904,709 A | 5/1999 | Arndt et al. | |
| 5,906,612 A | 5/1999 | Chinn | |
| 5,913,885 A | 6/1999 | Klatz et al. | |
| 5,916,242 A | 6/1999 | Schwartz | |
| 5,928,218 A * | 7/1999 | Gelbfish | 604/540 |
| 5,957,963 A | 9/1999 | Dobak, III | |
| 5,976,123 A | 11/1999 | Baumgardner et al. | |
| 6,007,514 A * | 12/1999 | Nita | 604/22 |
| 6,007,530 A * | 12/1999 | Dornhofer et al. | 606/1 |
| 6,030,412 A | 2/2000 | Klatz et al. | |
| 6,033,403 A | 3/2000 | Tu et al. | |
| 6,039,730 A | 3/2000 | Rabin et al. | |
| 6,041,787 A | 3/2000 | Rubinsky | |
| 6,042,579 A | 3/2000 | Eisberry et al. | |
| 6,045,532 A | 4/2000 | Eggers et al. | |
| 6,051,019 A | 4/2000 | Dobak, III | |
| 6,074,412 A | 6/2000 | Mikus | |
| 6,083,166 A | 7/2000 | Holdaway et al. | |
| 6,086,582 A | 7/2000 | Altman et al. | |
| 6,096,068 A | 8/2000 | Dobak, III | |
| 6,106,518 A | 8/2000 | Wittenberger et al. | |
| 6,120,500 A | 9/2000 | Bednarek et al. | |
| 6,126,684 A | 10/2000 | Gobin et al. | |
| 6,134,476 A | 10/2000 | Arndt et al. | |
| 6,143,019 A | 11/2000 | Motamedi et al. | |
| 6,149,677 A | 11/2000 | Dobak, III et al. | |
| 6,175,768 B1 | 1/2001 | Arndt et al. | |
| 6,182,666 B1 | 2/2001 | Dobak, III | |
| 6,203,540 B1 * | 3/2001 | Weber | 606/15 |
| 6,221,038 B1 * | 4/2001 | Brisken | 604/22 |
| 6,226,554 B1 | 5/2001 | Tu et al. | |
| 6,248,126 B1 | 6/2001 | Lesser et al. | |
| 6,280,441 B1 | 8/2001 | Ryan | |
| 6,283,959 B1 | 9/2001 | Lalonde et al. | |
| 6,358,247 B1 | 3/2002 | Altman et al. | |
| 6,379,371 B1 | 4/2002 | Novak et al. | |
| 6,386,202 B1 | 5/2002 | Frazee | |
| 6,413,263 B1 | 7/2002 | Lobdill et al. | |
| 6,416,510 B1 * | 7/2002 | Altman et al. | 606/41 |
| 6,440,129 B1 | 8/2002 | Simpson | |
| 6,443,969 B1 | 9/2002 | Novak et al. | |
| 6,447,507 B1 | 9/2002 | Bednarek et al. | |
| 6,451,012 B2 | 9/2002 | Dobak, III | |
| 6,505,629 B1 | 1/2003 | Mikus et al. | |
| 6,527,765 B2 | 3/2003 | Kelman et al. | |
| 6,527,767 B2 | 3/2003 | Wang et al. | |
| 6,546,932 B1 | 4/2003 | Nahon et al. | |
| 6,551,309 B1 | 4/2003 | LePivert et al. | |
| 6,565,556 B1 | 5/2003 | Korpan et al. | |
| 6,582,368 B2 | 6/2003 | Holdaway et al. | |
| 6,602,276 B2 | 8/2003 | Dobak, III et al. | |
| 6,648,880 B2 | 11/2003 | Chauvet et al. | |
| 6,663,554 B2 | 12/2003 | Babaev | |
| 6,689,086 B1 * | 2/2004 | Nita et al. | 604/22 |
| 6,702,811 B2 | 3/2004 | Stewart et al. | |
| 6,736,808 B2 | 5/2004 | Motamedi et al. | |
| 6,743,222 B2 | 6/2004 | Durkin et al. | |
| 6,786,902 B1 | 9/2004 | Rabin et al. | |
| 6,858,025 B2 | 2/2005 | Maurica | |
| 6,905,494 B2 | 6/2005 | Yon et al. | |
| 6,936,024 B1 | 8/2005 | Houser | |
| 6,936,045 B2 | 8/2005 | Yu et al. | |
| 6,960,206 B2 | 11/2005 | Keane | |
| 7,001,378 B2 | 2/2006 | Yon et al. | |
| 7,041,095 B2 | 5/2006 | Wang et al. | |
| 7,135,029 B2 | 11/2006 | Makin et al. | |
| 7,137,977 B2 | 11/2006 | Brucker et al. | |
| 7,220,257 B1 | 5/2007 | Lafontaine | |
| 7,238,180 B2 | 7/2007 | Mester et al. | |
| 2001/0007940 A1 * | 7/2001 | Tu et al. | 606/41 |
| 2003/0100911 A1 * | 5/2003 | Nash et al. | 606/159 |
| 2003/0204199 A1 | 10/2003 | Novak et al. | |
| 2004/0102769 A1 | 5/2004 | Schwartz et al. | |
| 2004/0162571 A1 | 8/2004 | Rabiner et al. | |
| 2004/0176755 A1 | 9/2004 | Lafontaine | |
| 2004/0249372 A1 | 12/2004 | Capuano et al. | |
| 2005/0038420 A1 | 2/2005 | Huybregts et al. | |
| 2005/0154409 A1 | 7/2005 | MacKool | |
| 2005/0245951 A1 | 11/2005 | Nita et al. | |
| 2005/0288654 A1 | 12/2005 | Nieman et al. | |
| 2007/0088217 A1 | 4/2007 | Babaev | |

OTHER PUBLICATIONS

Kullervo Hynynen, et al., Cylindrical Ultrasound Transducers for Cardiac Catheter Ablation, IEEE Transactions on Biomedical Engineering, Feb. 1997, pp. 144-151, vol. 44, No. 2.

Mathew R. Williams, et al., alternative Energy Sources for Surgical Atrial Ablation, J. Card Surg 2004; vol. 19, pp. 201-206, Columbia College of Physicians and Surgeons, Division of Cardiothoracic Surgery, Surgical Arrhythmia Program, New York, NY.

* cited by examiner

ABLATIVE ULTRASONIC-CRYOGENIC APPARATUS

CROSS REFERENCE TO RELATED APPLICATIONS

This application is a continuation-in-part of U.S. patent application Ser. No. 11/463,187, filed Aug. 8, 2006, which is now abandoned.

BACKGROUND OF THE INVENTION

1. Field of the Invention

The present invention relates to an ablative apparatus that can be used to treat atrial fibrillation and/or other cardiac arrhythmias by ablating cardiac tissue.

2. Description of the Related Art

Accounting for one-third of the hospitalizations for cardiac arrhythmia, atrial fibrillation (AF) is the most common arrhythmia (abnormal beating of the heart) encountered in clinical practice. (ACC/AHA/ESC Guidelines for the Management of Patients With Atrial Fibrillation) AF is a specific type of arrhythmia in which an abnormal beating of the heart originates in one of the heart's two atrium. Increasing in prevalence, an estimated 2.2 million Americans suffer from AF. (ACC/AHA/ESC Guidelines for the Management of Patients With Atrial Fibrillation) Underlying one out of every six strokes, AF doubles the rate of morbidity compared to patients with normal sinus rhythm. (ACC/AHA/ESC Guidelines for the Management of Patients With Atrial Fibrillation) Further increasing the clinical severity, the presence of AF leads to functional and structural changes in the atrial myocardium (cells responsible for the beating of the heart) that favors its maintenance. As such, AF is a serious disorder requiring medical intervention.

Administering drugs that alter the electrical properties of atrial myocardium has been effective in treating less severe cases of AF. (Hurst's the heart, page 836) However, such drugs often lead to the creation of pro-arrhythmic conditions thereby resulting in the treatment of one type of arrhythmia only to create another. Due to the increased risk of stroke, it is advised that all patients with AF, despite the successfulness of drug therapy, be prescribed warfarin or other anticoagulants to inhibit the formation of blood clots. (Hurst's the heart, page 833) Besides being difficult to dose, warfarin has several complications associated with its long term use. Altering the metabolism of other drugs, warfarin is known to induce several adverse interactions with other medications commonly prescribed to elderly patients, who are at increased risk of developing AF.

AF originates in regions of myocardium contracting, or beating, out of step with the rest of the heart. Heart cells contract in response to electrical stimulation. In a healthy heart, the electrical stimulation signaling contraction originates from the sinus node (the heart's natural pace maker) and spreads in an organized manner across the heart. In a heart plagued with AF, a region of myocardium elicits a mistimed contraction, or heart beat, on its own or in response to an electrical signal generated from somewhere other than the sinus node. Generating an electrical signal, the mistimed contraction spreads across the heart, inducing contractions in neighboring regions of the heart. Inducing the formation of scar tissue on the heart by ablating, cutting, or otherwise injuring tissue in regions in which AF originates has been shown to be affective in treating AF. The logic behind this treatment is to terminate AF by removing the heart cells responsible for its presence, while preserving healthy cells. Creating scar tissue barriers as to prevent the spread of electrical signals from mistimed contractions has also been shown to be effective in treating AF. (Hurst's the heart, page 838)

Successful surgical intervention eliminates the need for continued warfarin treatment in most patients. (Hurst's the heart, page 839) Initially surgical treatment was reserved for patients undergoing additional cardiac surgery, such as valve repair or replacement. (Hurst's the heart, page 838) The high success rate and efficacy of surgical intervention in the treatment of AF has spurred the development of cardiac catheters capable of therapeutically ablating cardiac tissue without the need for open chest or open heart surgery.

Heart surgery preformed by means of catheter involves, in it basic conception, the insertion of a catheter either into a patient's vein or chest cavity. The catheter is then advanced to the heart. When the catheter is inserted into a patient's vein, the catheter is advanced into one of the heart's four chambers. When the catheter in inserted into a patient's chest, the catheter is advanced to the outer walls of the patient's heart. After the catheter reaches the patient's heart the surgeon utilizes the catheter to ablate, damage or, kill cardiac tissue. The ideal catheter induced lesion is one that is created from the epicardium (outside) of the beating heart, is able to go through epicardial fat, is performed rapidly over variable lengths, is transmural, causes no collateral injury, and can be applied at any desired anatomic location. (Williams et al., 2004) Ablating cardiac tissue by heating the tissue to 50 degrees Celsius has become the preferred means of inducing lesions (Williams et al., 2004). Cardiac catheters employing a variety of thermal ablative energy sources have been developed, none of which are capable of inducing an ideal lesion.

Catheters utilizing radio frequency as an ablative energy source, the current gold standard, are incapable of creating an ideal lesion. (Cummings et al., 2005) In particular, radio frequency catheters have a difficult time creating ablations through the epicardial fat surrounding the heart. Furthermore, inducing deep lesions with radio frequency is not possible without inflicting collateral damage from surface burning and steam popping. (Cummings et al., 2005) Steam popping is the phenomenon in which cells become heated to such a point their internal fluids begin to boil, producing steam that bursts the cell. Simultaneously cooling the site of radio frequency administration reduces the incidence of surface burns but does not reduce the risk of steam popping. (Cummings et al., 2005) In an effort to overcome the shortcomings of radio frequency induced lesions, catheters employing novel energy sources have been developed.

In hopes that microwaves would provide sufficiently deep lesions, catheters employing microwaves as an ablative energy source have been developed. Because the penetration of microwaves into tissue has a steep exponential decline, it has been found necessary to bring the catheter into close contact with the tissue in order to induce deep lesions. (Cummings et al., 2005) Furthermore, fat continues to be a significant barrier. (Williams et al., 2004)

Lasers have also been applied as an ablative energy source within catheters. Although high powered lasers carry a high risk of crater formation at the site of application, low energy lasers produce lesions with a depth related to the duration of application. (Cummings et al., 2005)

Capable of penetrating fat and inducing fasts lesion at specific depths when focused, high intensity ultrasound has been predicted to be an advantageous source of ablative energy in catheters. (Williams et al., 2004)

An alternative to ablation by heating is the practice of ablating tissue by freezing. Severe cold, also know cryogenic energy, as an ablative energy source has the advantages of avoiding clot formation. (Williams et al., 2004) Another advantage of catheters employing cryogenic energy is the ability to temporary paralyze regions of myocardium tissue as to test the benefit of a planned lesion. When a region of tissue is paralyzed by freezing it can no longer initiate an arrhythmia. If paralyzing a region of the heart completely or partial restores a normal heart beat, the surgeon knows she has her catheter aimed at the right spot.

SUMMARY OF THE INVENTION

An ablative apparatus that can be used to ablate cardiac tissue is disclosed. The ablative apparatus comprises an ablation probe, a transducer capable of ultrasonically driving the ablation probe in contact with the proximal end of the ablation probe, a guide wire secured at one end to the transducer and/or ablation probe, electrical leads running along the guide wire and connected to electrodes capable of exposing piezo ceramic discs within the transducer to an alternating voltage, a catheter encasing the ablation probe, transducer, and at least a portion of the guide wire, and a handle secured to the end of the guide wire opposite the transducer. Preferably, the catheter is composed of a biologically compatible polymer.

The ablation probe located at the distal end of the catheter system may comprise a proximal surface, a distal surface opposite the proximal surface, at least one radial surface extending between the proximal surface and the distal surface, and at least one abrasive member on at least one surface other than the proximal surface. As the distal end of the ablative apparatus is advanced towards the heart, the ablation probe may be contained within a pocket at the distal end of the catheter. When the distal end of the catheter reaches the tissue to be ablated, the ablation probe may be removed from the pocket, as to expose the abrasive member(s). When the transducer in contact with the proximal surface of the ablation probe is activated by supplying it with an electrical current, the ablation probe becomes driven by ultrasonic energy generated by the transducer and begins to vibrate. As the ablation probe vibrates, the abrasive members on the ablation probe scratch tissues with which the members come in contact, as to create an abrasion in the tissues. Physically inducing an abrasion within a tissue, the vibrating ablation probe is capable of mechanically ablating tissues. When the ablation probe is advanced to the heart, mechanical ablation may be utilized to penetrate epicardial fat, thereby exposing the underlying myocardium. The exposed myocardium may then be subjected to mechanical ablation, cryoablation, ultrasonic ablation, and/or any combination thereof.

Flowing a cryogenic material through the catheter, as to deliver cryogenic energy to the ablation probe, to a region of the catheter in close proximity to the ablation probe, and/or to another region of the catheter, may enable cryoablation. Lumens running substantially the length of the catheter and joined by a junction may enable a cryogenic material to flow through the catheter. Such lumens may comprise a cryogenic intake lumen originating at the proximal end of the catheter and running substantially the length of the catheter, through which a cryogenic material flows from the proximal end of the catheter towards its distal end. Likewise, a cryogenic exhaust lumen running substantially the length of the catheter and substantially parallel to the cryogenic intake lumen and terminating at the proximal end of the catheter may permit a cryogenic material to flow towards the proximal end of the catheter. A junction at the distal end of the intake lumen and exhaust lumen connecting the lumens may permit a cryogenic material to be exchanged between the lumens. The cryogenic material may be prevented from exiting the catheter by a partition distal to the junction isolating the intake lumen and exhaust lumen from the remaining distal portions of the catheter. Thus, a cryogenic material may be flowed through the catheter by first flowing through an intake lumen and towards the distal end of the catheter. The cryogenic material then exits the intake lumen and enters the exhaust lumen at a junction connecting the lumens. Completing its flow through the catheter, the cryogenic material then flows through the exhaust lumen and back towards the proximal end of the catheter.

Cryogenic ablation may also be enabled by flowing a cryogenic material through the guide wire. As with the catheter, lumens running substantially the length of the guide wire and joined by a junction may enable a cryogenic material to flow through the guide wire. Such lumens may comprise cryogenic intake lumen originating at the proximal end of the guide wire and running substantially the length of the wire, through which a cryogenic material flows from the proximal end of the guide wire towards its distal end. Likewise, a cryogenic exhaust lumen running substantially the length of the wire and substantially parallel to the cryogenic intake lumen and terminating at the proximal end of the wire may permit a cryogenic material to flow towards the proximal end of the wire. A junction at the distal end of the intake lumen and exhaust lumen connecting the lumens may permit a cryogenic material to be exchanged between the lumens. The junction connecting the lumens may comprise a chamber internal to the ablation probe into which the intake lumen and exhaust lumen open. Thus, a cryogenic material may be flowed through the guide wire by first flowing through an intake lumen and towards the distal end of the wire. The cryogenic material then exits the intake lumen and enters the exhaust lumen at a junction connecting the lumens. Completing its flow through the wire, the cryogenic material then flows through the exhaust lumen and back towards the distal end of the catheter.

Regardless of whether a cryogenic material is flowed through the catheter or guide wire, the ablative apparatus enables the surgical treatment of cardiac arrhythmias by providing a means to mechanically, ultrasonically, and/or cryogenically ablate myocardial tissue. As such, a surgeon utilizing the disclosed ablative apparatus will be able to select the appropriate ablative means or combination of ablative means best suited for the patient's particular pathology and the type of lesion the surgeon wishes to induce. Driving the ablation probe with ultrasound energy generated by the transducer enables a surgeon to quickly induce surface abrasions of various depths by adjusting the pulse frequency and duration of the driving ultrasound. This may prove advantageous when the surgeon wishes to induce a lesion at a specific location with minimal collateral injury, such as during AV nodal modification.

Combining ultrasonic energy with cryogenic energy, the ablative apparatus may enable the surgeon to cryoablate tissue without the ablation probe adhering to the tissue being ablated. As such, the surgeon may be able to easily move the probe during ablation. The ablation probe may be moved during the induction of a lesion by including control means for steering and/or rotating the ablation probe within the handle. The probe's mobility during cryoablation could allow the surgeon to create linear lesions in cardiac tissue or isolating lesions in vessel walls. Thus, by combining ultrasonic and cryogenic energy the ablative apparatus may give the surgeon greater control over the lesion induced. Furthermore, it has been hypothesized that the administration of low frequency ultrasound and cryoablation induces the release of several healing factors from the targeted tissue. Therefore, ultrasonically vibrating the ablation probe during cryoablation may improve mobility of the ablation probe and possibly induce healing.

Alternatively or in combination, dually administering ultrasonic energy and cryogenic energy may protect surface tissue during the administration of a deep lesion, thereby limiting collateral damage. During the cryogenic induction of a deep lesion, the co-administration of ultrasonic energy will warm the surface tissue preventing it from freezing. Likewise, administering cryogenic energy during the induction of a deep lesion with ultrasonic energy will cool surface tissue thereby protecting it from ablative cavitation, possibly by reducing molecular movement.

In the alternative or in combination, the ablative apparatus may also enable the surgeon to deliver various drugs and/or other pharmacological compounds to the location of the lesion and/or other locations. Combining drug delivery with the application of ultrasound energy may assist drug delivery and drug penetration into the targeted tissue. Delivering an antithrombolytic during the induction of a lesion may reduce the likelihood of clot formation, especially during mechanical ablation. The surgeon may also choose to expedite healing by delivering various healing and/or growth factors to the site of the lesion.

Drug delivery may be accomplished by coating the ablation probe with a drug or other pharmacological compound. When so coated, driving the ablation probe with ultrasonic energy may liberate the drug coating from the probe and embed it within the targeted tissue. In the alternative or in combination, the catheter may contain a drug lumen and/or reservoir permitting the administration of a drug to internal locations of the patient's body.

BRIEF DESCRIPTION OF THE DRAWINGS

The ablative apparatus will be shown and described with reference to the drawings of preferred embodiments and clearly understood in detail.

DETAILED DESCRIPTION OF THE INVENTION

Disclosed is an ablative apparatus that may be used to treat atrial fibrillation and other arrhythmias. Preferred embodiments of the ablative apparatus are illustrated in the figures and described in detail below.

Figure 1:
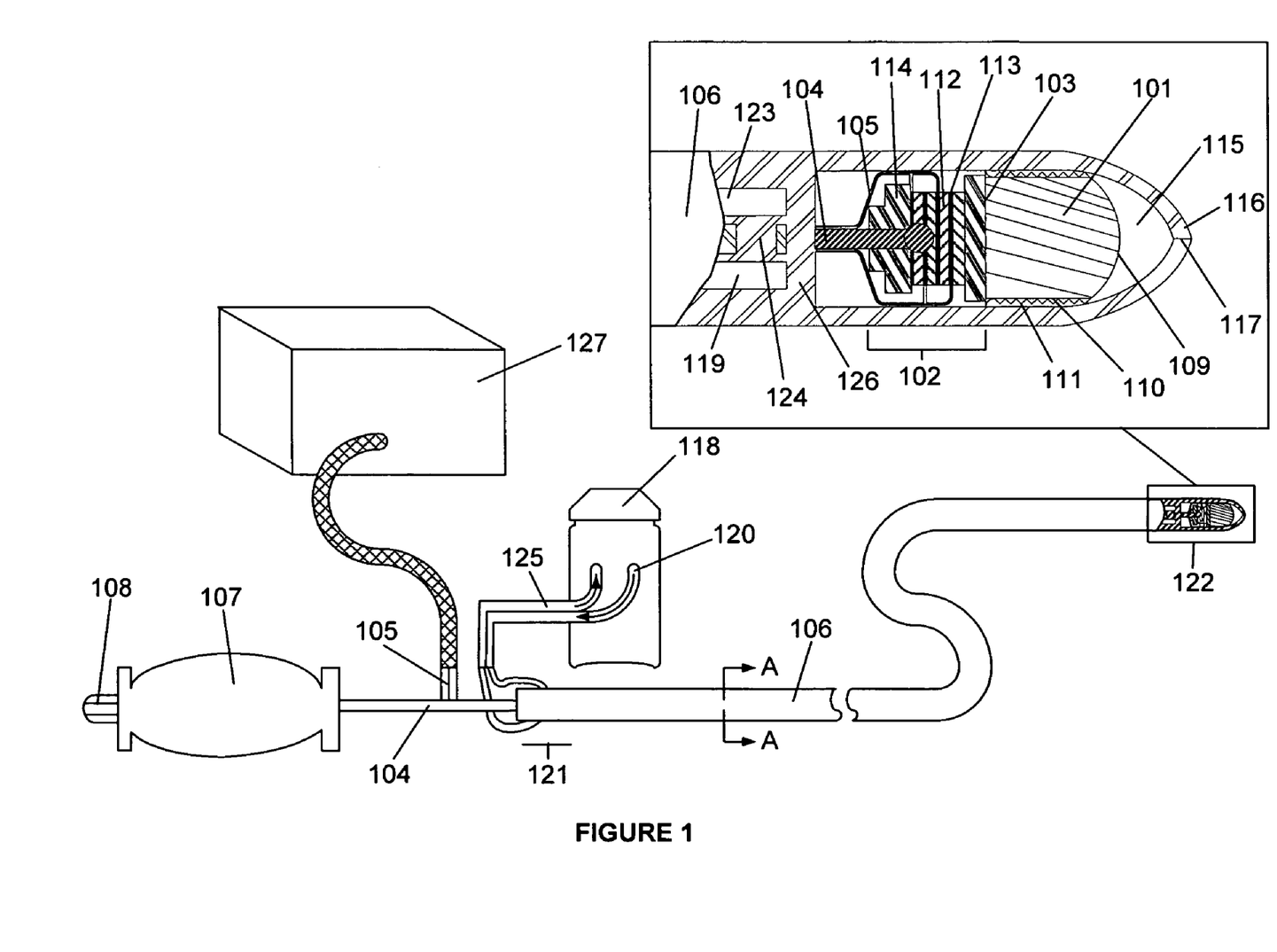
FIG. 1 depicts a possible embodiment of the ablative apparatus.

FIG. 1 depicts a possible embodiment of the ablative apparatus. The ablative apparatus comprises an ablation probe 101, a transducer 102 capable of capable of ultrasonically driving the ablation probe 101 in contact with the proximal surface 103 of ablation probe 101, a guide wire 104 secured at one end to transducer 102, electrical leads 105 running along guide wire 104 and connected to electrodes 113 capable of exposing piezo ceramic disc 112 within transducer 102 to an alternating voltage, a catheter 106 encasing ablation probe 101, transducer 102, and at least a portion of guide wire 104, and a handle 107 secured to the end of guide wire 104 opposite transducer 102. Preferably, catheter 106 is composed of a biologically compatible polymer. Handle 107 may contain control means 108 for steering and/or rotating ablation probe 101. Exemplar control means have been described in U.S. Pat. Nos. 4,582,181 and 4,960,134, the teachings of which are incorporated herein by reference. In addition to housing control means, handle 107 may provide a means of rotating ablation probe 102. When rotated, ablation probe 101 moves in a circular motion similar to the manner in which the hands of clock move about its face. Rotation of ablation probe 101 can be accomplished by the surgeon turning handle 107 with his wrist as if he were using a screw driver. Extending from handle 107, through catheter 106, to transducer 102, guide wire 104 provides rigidity to catheter 106. Guide wire 104 may also carry electrical leads 105 down catheter 106 to transducer 101. Transmitting an electrical current generated by generator 127 to transducer 102, electrical leads 105 energize transducer 102 as to drive ablation probe 101.

In keeping with FIG. 1, a portion of the distal end 122 of catheter 106 has been cut away as to expose ablation probe 101 and transducer 102. Ablation probe 101 comprises a distal surface 109, a proximal surface 103 opposite the distal surface 109, at least one radial surface 110 extending between distal surface 109 and proximal surface 103, and abrasive members 111 on radial surface 110. Transducer 102, in contact with the proximal surface 103 of ablation probe 101, comprises a stack of piezo ceramic discs 112 arranged in a manner similar to that of a roll of coins. Running from generator 127 to electrodes 113, electrical leads 105 carry a current to electrodes 113 as to expose piezo ceramic discs 112 to an alternating voltage. So energizing transducer 102 induces the expansion and contraction of piezo ceramic discs 112, as to drive ablation probe 101. Expanding and contracting, piezo ceramic discs 112 apply ultrasonic energy to ablation probe 101. Applying ultrasonic energy to probe 101 may induce a vibrating or oscillating movement of probe 101. As ablation probe 101 moves, abrasive members 111 scratch tissues with which the members 111 come in contact, as to create an abrasion in the tissue. Back drive 114, located at the proximal end of transducer 102, stabilizes ablation probe 101 when it is driven by ultrasound energy generated by transducer 102.

Continuing with FIG. 1, catheter 106, encasing ablation probe 101, transducer 102, and a portion of guide wire 104, contains a pocket 115 at its distal end 122 encasing ablation probe 101. Encasing ablation probe 101 within pocket 115 may enable the distal end of the ablative apparatus to be advanced towards the tissue to be ablated without abrasive members 111 damaging tissue. When the distal end 122 of the catheter 106 reaches the tissue to be ablated, ablation probe 101 may be removed from pocket 115, as to expose abrasive members 111, by firmly pulling catheter 106 towards handle 107. As to facilitate the penetration of the sealed tip 116 at the distal end of pocket 115 by ablation probe 101, sealed tip 116 may contain single or multiple slits 117. Slit(s) 117 may completely or partially penetrate sealed tip 116. Conversely, firmly pulling handle 107 away from the patient while catheter 106 is held stationary returns ablation probe 101 to the inside of pocket 115. Advancing the ablative apparatus into and through the patient's body with ablation probe 101 retracted within pocket 115 protects the patient's internal tissues from damage by abrasive members 111. When ablation probe 101 has been advanced to the desired location, the surgeon may retract catheter 106, exposing ablation probe 101. The surgeon may then mechanically ablate the target tissue by driving ablation probe 101 with ultrasound energy generated by transducer 102. Alternatively, the surgeon may not expose ablation probe 101, but rather induce a lesion with low frequency ultrasound energy and/or cryogenic energy.

In keeping with FIG. 1, flowing a cryogenic material through catheter 106, as to deliver cryogenic energy to ablation probe 101, to a region of catheter 106 in close proximity to ablation probe 101, and/or to another region of catheter 106, may enable cryoablation. A cryogenic material may be delivered to catheter 106 from a cryogenic storage and retrieval unit 118 in fluid communication with cryogenic intake lumen 119 via cryogenic feed tubing 120, attached to the proximal end intake lumen 119. Originating at the proximal end 121 of catheter 106 and running substantially the length of catheter 106, cryogenic intake lumen 119 permits a cryogenic material entering catheter 106 from storage and retrieval unit 118 to flow towards the distal end 122 of catheter 106. After reaching the distal end of intake lumen 119, the cryogenic material flows through a junction connecting intake lumen 119 with exhaust lumen 123 located at the distal end of the intake lumen 119 and exhaust lumen 123. The specific junction depicted in FIG. 1 comprises a port 124 between intake lumen 119 and exhaust lumen 123. Running substantially the length of catheter 106, substantially parallel to intake lumen 119, and terminating at the proximal end 121 of catheter 106, exhaust lumen 123 permits the cryogenic material to flow towards proximal end 121 of catheter 106. After reaching the proximal end 121 of catheter 106, the cryogenic material is returned to storage and retrieval unit 118 via cryogenic exhaust tubing 125 attached to the proximal end exhaust lumen 123, which is in fluid communication with storage and retrieval unit 118 and exhaust lumen 123. Cryogenic storage and retrieval may alternatively be accomplished by the simultaneous use of separate storage and retrieval units. The storage and retrieval unit may also permit the recycling of the employed cryogenic material as to reduce operation costs.

As to prevent the cryogenic material from entering pocket 115 and/or exiting catheter 106, a partition 126 distal to port 124 isolates intake lumen 119 and exhaust lumen 123 from pocket 115.

In order to prevent catheter 106 from becoming rigid and inflexible as cryogenic material flows through it, catheter 106, or portion thereof, may be wrapped with a wire conducting an electrical current. The resistance in the wire to the flow of electricity may generate heat that warms catheter 106, thereby keeping it flexible. Alternatively, the warming wire may be wrapped around guide wire 104.

Disclosed in U.S. patent application Ser. No. 11/454,018, entitled Method and Apparatus for Treating Vascular Obstructions, and filed Jul. 15, 2006, are exemplar configurations of catheter that may be used in the alternative to catheter 106. The teachings of U.S. patent application Ser. No. 11/454,018 are hereby incorporated by reference.

Figure 2:
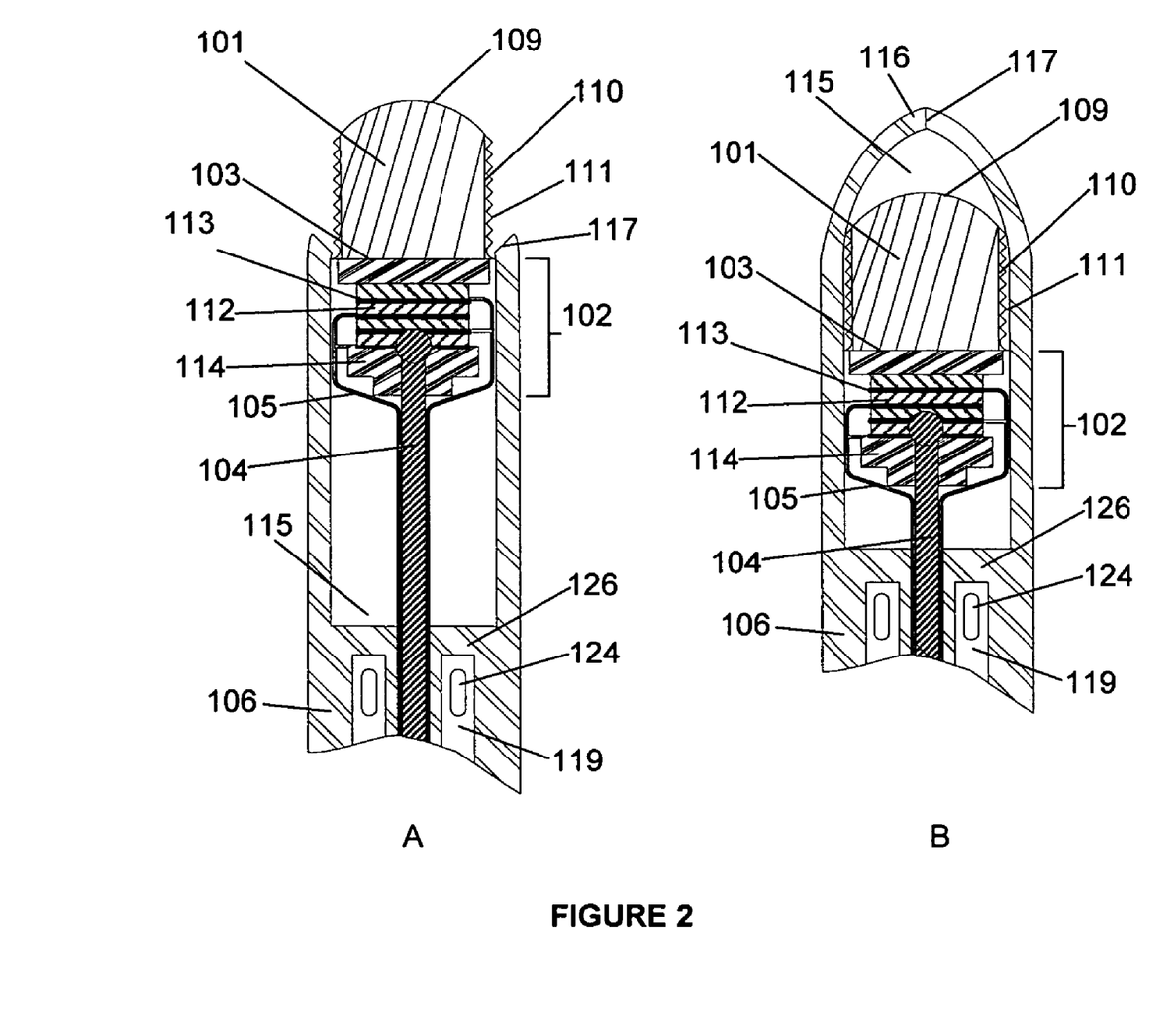
FIG. 2 depicts cross-sectional views of the proximal end of the embodiment of the ablative apparatus depicted in FIG. 1.

FIG. 2 depicts cross-sectional views of the proximal end of the embodiment of the ablative apparatus depicted in FIG. 1. FIG. 2A depicts a cross-sectional view of the embodiment of the apparatus depicted in FIG. 1 with ablation probe 101 extended from pocket 115. FIG. 2B depicts a cross-sectional view of the embodiment of the apparatus depicted in FIG. 1 with ablation probe 101 retracted into pocket 115. As previously stated in the discussion of FIG. 1, catheter 106 comprises a cryogenic intake lumen 119 and an exhaust lumen 123 (obscured in the present view by intake lumen 119) connected by ports 124. The flow of a cryogenic material from the proximal end 121 of catheter 106 towards the distal end 122 of catheter 106 through intake lumen 119, across ports 124, and then back towards the proximal end 121 through exhaust lumen 123 cools pocket 115. Flowing adjacent to or in close proximity to ablation probe 101 and/or transducer 102, the cryogenic material flowing through catheter 106 may also cool ablation probe 101 and/or transducer 102. It should be appreciated that in the alternative to the ports depicted in FIGS. 1 and 2, the junction between the intake lumen 119 and exhaust lumen 123 may comprise a chamber.

Figure 3:
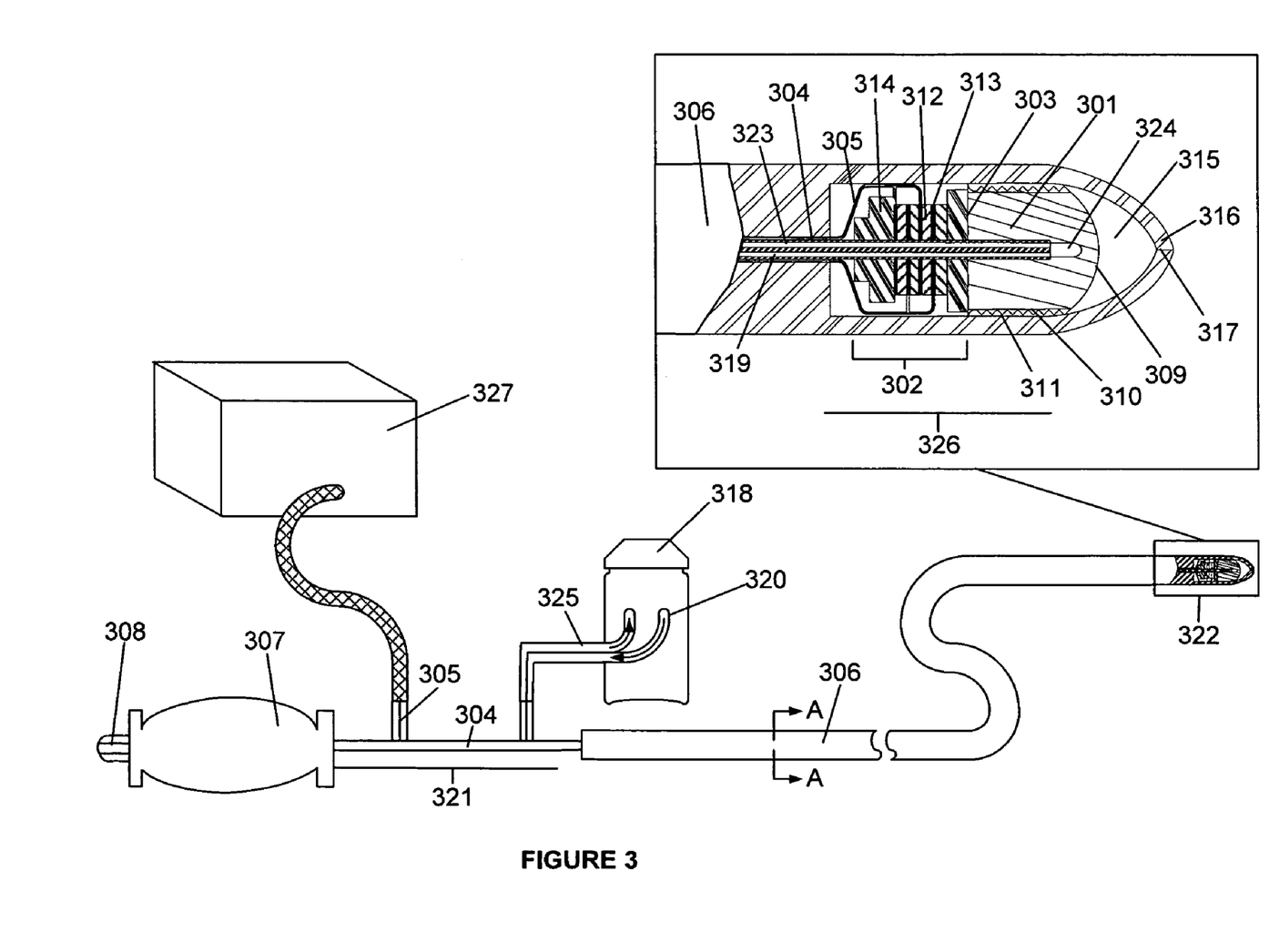
FIG. 3 depicts an alternative embodiment of the ablative apparatus.

FIG. 3 depicts an alternative embodiment of the ablative apparatus. The depicted embodiment of the ablative apparatus comprises an ablation probe 301, a transducer 302 capable of ultrasonically driving the ablation probe 301 in contact with the proximal surface 303 of ablation probe 301, a guide wire 304 secured at one end to ablation probe 301 and/or transducer 302, electrical leads 305 running along guide wire 304 and connected to electrodes 313 capable exposing piezo ceramic disc 312 within transducer 302 to an alternating voltage, a catheter 306 encasing ablation probe 301, transducer 302, and at least a portion of guide wire 304, and a handle 307 secured to the end of guide wire 304 opposite ablation probe 301. Handle 307 may contain control means 308 for steering and/or rotating ablation probe 301. Exemplar control means have been described in U.S. Pat. Nos. 4,582, 181 and 4,960,134, the teachings of which were previously incorporated herein by reference. In addition to housing control means, handle 308 may provide a means of rotating ablation probe 301. As with the embodiment depicted in FIG. 1, the rotation of ablation probe 301 can be accomplished by the surgeon turning handle 307 with his wrist as if he were using a screw driver. Extending from handle 307, through catheter 306, to ablation probe 301, guide wire 304 provides rigidity to catheter 306. Guide wire 304 may also carry electrical leads 305 down catheter 306 to transducer 302. Transmitting an electrical current generated by generator 327 to transducer 302, electrical leads 305 energize transducer 302 as to drive ablation probe 301.

In keeping with FIG. 3, a portion of the distal end 322 of catheter 306 has been cut away as to expose ablation probe 301 and transducer 302. Ablation probe 301 comprises a distal surface 309, a proximal surface 303 opposite the distal surface 309, at least one radial surface 310 extending between distal surface 309 and proximal surface 303, and abrasive members 311 on radial surface 310. Transducer 302, in contact with the proximal surface 303 of ablation probe 301 and encircling guide wire 304, comprises a stack of piezo ceramic discs 312 arranged in a manner similar to that of a roll of coins. Running from generator 327 to electrodes 313, electrical leads 305 carry a current to electrodes 313 as to expose piezo ceramic discs 312 to an alternating voltage. So energizing transducer 302 induces the expansion and contraction of piezo ceramic discs 312, as to drive ablation probe 301. Expanding and contracting, piezo ceramic discs 312 apply ultrasonic energy to ablation probe 301. Applying ultrasonic energy to probe 301 may induce a vibrating or oscillating movement of probe 301. As ablation probe 301 moves, abrasive members 311 scratch tissues with which the members 311 come in contact, as to create an abrasion in the tissue. Back drive 314, located at the proximal end of transducer 302, stabilizes ablation probe 301 when it is driven by ultrasound energy generated by transducer 302.

Continuing with FIG. 3, catheter 306, encasing ablation probe 301, transducer 302, and a portion of guide wire 304, contains a pocket 315 at its distal end 322 encasing ablation probe 301. Encasing ablation probe 301 within pocket 315 may enable the distal end of the ablative apparatus to be advanced towards the tissue to be ablated without abrasive members 311 damaging tissue. When the distal end 322 of the catheter 306 reaches the tissue to be ablated, ablation probe 301 may be removed from pocket 315, as to expose abrasive members 311, by firmly pulling catheter 306 towards handle 307. As to facilitate the penetration of the sealed tip 316 at the distal end of pocket 315 by ablation probe 301, sealed tip 316 may contain single or multiple slits 317. Slit(s) 317 may completely or partially penetrate sealed tip 316. Conversely, firmly pulling handle 307 away from the patient while holding catheter 306 stationary returns ablation probe 301 to the inside of pocket 315. Advancing the ablative apparatus into and through the patient's body with ablation probe 301 retracted within pocket 315 protects the patient's internal tissues from damage by abrasive members 311. When ablation probe 301 has been advanced to the desired location, the surgeon may retract catheter 306, exposing ablation probe 301. The surgeon may then mechanically ablate the target tissue by driving ablation probe 301 with ultrasound energy generated by transducer 302. Alternatively, the surgeon may not expose ablation probe 301, but rather induce a lesion with low frequency ultrasound energy and/or cryogenic energy.

In keeping with FIG. 3, flowing a cryogenic material through guide wire 304, as to deliver cryogenic energy to ablation probe 301, may enable cryoablation. A cryogenic material may be delivered to guide wire 304 from a cryogenic storage and retrieval unit 318 in fluid communication with cryogenic intake lumen 319 via cryogenic feed tubing 320, attached to the proximal end intake lumen 319. Originating at the proximal end 321 of guide wire 304 and running substantially the length of guide wire 304, cryogenic intake lumen 319 permits a cryogenic material entering guide wire 304 from storage and retrieval unit 318 to flow towards the distal end 326 of guide wire 304. After reaching the distal end of intake lumen 319, the cryogenic material flows through a junction connecting intake lumen 319 with exhaust lumen 323 at the distal end of the intake lumen 319 and exhaust lumen 323. The specific junction depicted in FIG. 3 comprises an expansion chamber 324 within ablation probe 301 into which intake lumen 319 and exhaust lumen 323 open. Running substantially the length of guide wire 304, substantially parallel to intake lumen 319, and terminating at the proximal end 321 of guide wire 304, exhaust lumen 323 permits the cryogenic material to flow towards proximal end 321 of guide wire 304. After reaching the proximal end 321 of guide wire 304, the cryogenic material is returned to storage and retrieval unit 318 via cryogenic exhaust tubing 325 attached to the proximal end exhaust lumen 323, which is in fluid communication with storage and retrieval unit 318 and exhaust lumen 323. Cryogenic storage and retrieval may alternatively be accomplished by the simultaneous use of separate storage and retrieval units. The storage and retrieval unit may also permit the recycling of the employed cryogenic material as to reduce operation costs.

In order to prevent catheter 306 from becoming rigid and inflexible as cryogenic material flows through guide wire 304, catheter 306, or portion thereof, may be wrapped with a wire conducting an electrical current. The resistance in the wire to the flow of electricity may generate heat that warms catheter 306, thereby keeping it flexible. Alternatively, the warming wire may be wrapped around guide wire 304.

Figure 4:
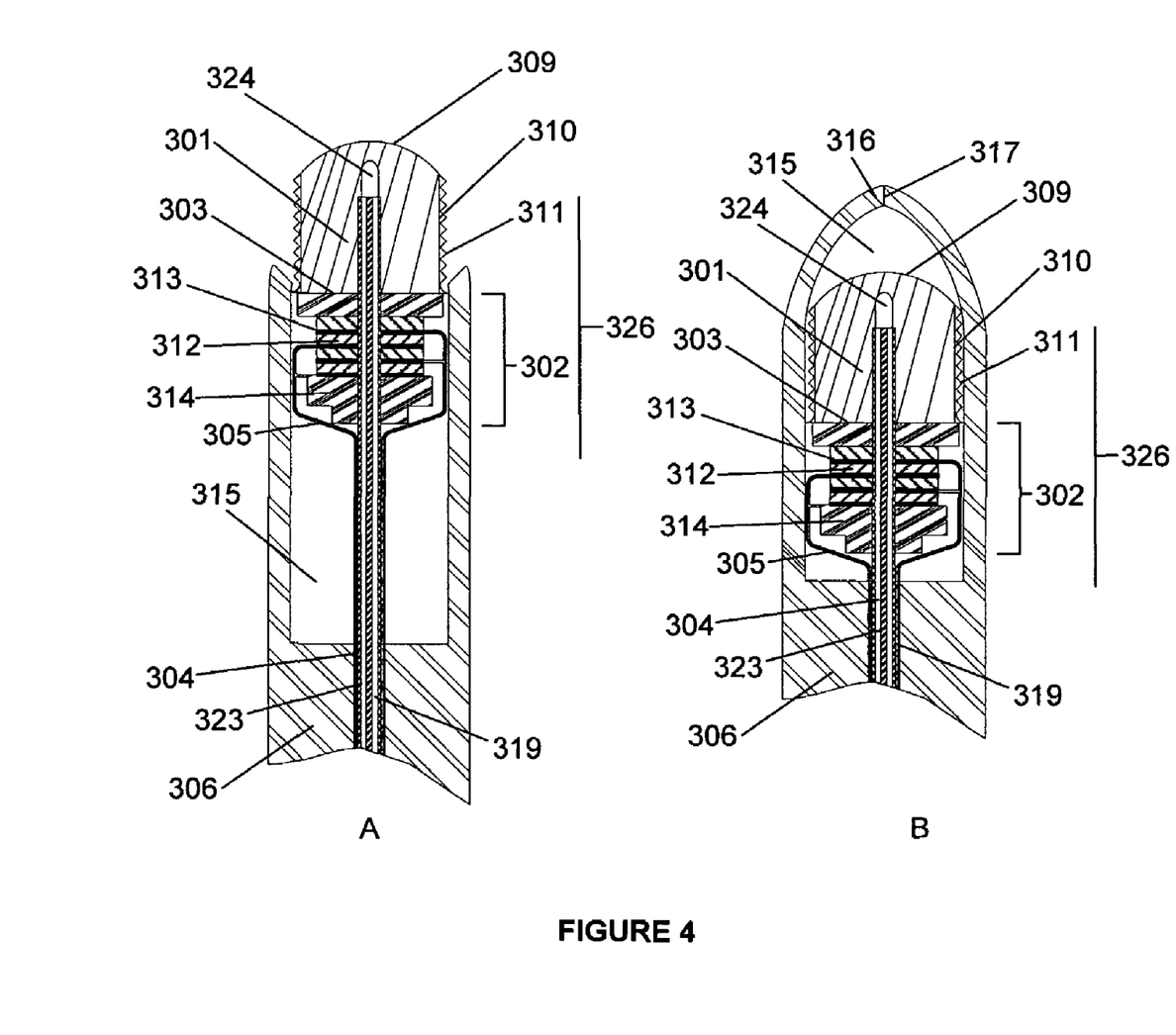
FIG. 4 depicts cross-sectional views of the proximal end of the embodiment of the ablative apparatus depicted in FIG. 3.

FIG. 4 depicts cross-sectional views of the proximal end of the embodiment of the ablative apparatus depicted in FIG. 3. FIG. 4A depicts a cross-sectional view of the embodiment of the apparatus depicted in FIG. 3 with ablation probe 301 extended from pocket 315. FIG. 4B depicts a cross-sectional view of the embodiment of the apparatus depicted in FIG. 3 with ablation probe 301 retracted into pocket 315. As previously stated in the discussion of FIG. 3, guide wire 304 comprises a cryogenic intake lumen 319 and an exhaust lumen 323 connected by expansion chamber 324. The flow of a cryogenic material from the proximal end 321 of guide wire 304 towards the distal end 326 of guide wire 304 through intake lumen 319, across the junction formed by expansion chamber 324, and then back towards the proximal end 321 through exhaust lumen 323 cools ablation probe 301. Expansion chamber 324 may be located within ablation probe 301, as depicted in FIGS. 3 and 4. Alternatively, expansion chamber 324 may be located within transducer 302 and could, but need not, extend into ablation probe 301. It should be appreciated that in the alternative to the expansion chamber depicted in FIGS. 3 and 4, the junction between the intake lumen 319 and exhaust lumen 323 may comprise one or a series of ports connecting intake lumen 319 with exhaust lumen 323.

Incorporating threading on a portion of the ablation probe and/or transducer along with corresponding threading on the internal surface of the catheter's pocket may facilitate a smooth deployment of the ablation probe from the catheter's pocket. In such an embodiment, the surgeon would advance the ablation probe from the pocket by rotating the guide wire and attached ablation probe. Rotating the guide wire in the opposite direction would retract the ablation probe back into the pocket.

The ablation probe of the ablative apparatus may contain one or multiple abrasive members attached to its proximal and/or radial surfaces. Furthermore, the abrasive members may be constructed in various configurations, as depicted in FIG. 5.

Figure 5:
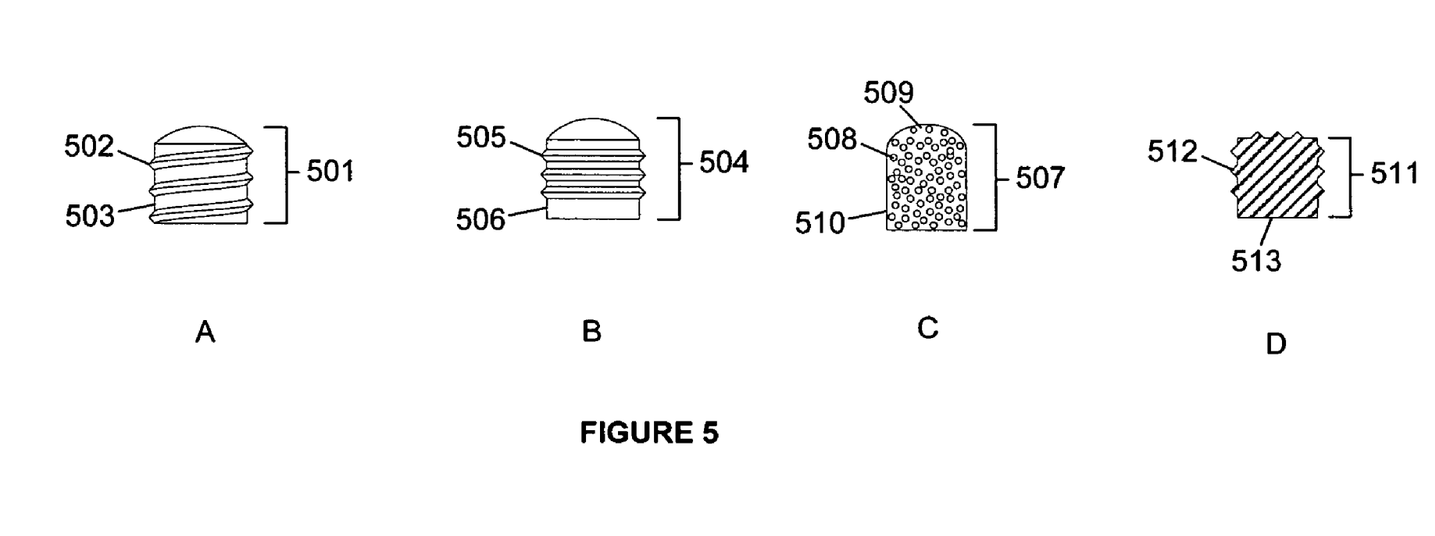
FIG. 5 depicts various ablation probes each comprising a distal surface, a proximal surface opposite the distal surface, a radial surface extending between the proximal surface and the distal surface, and abrasive members on a surface other than the proximal surface.

FIG. 5 depicts various ablation probes each comprising a distal surface, a proximal surface opposite the distal surface, and a radial surface extending between the proximal surface and the distal surface, and abrasive members on a surface other than the proximal surface. The ablation probe 501, depicted in FIG. 5A, contains an abrasive member comprising a thin band 502 attached to radial surface 503 and spiraling around ablation probe 501 similar to the threads of a screw. Alternatively, the ablation probe 504, as depicted in FIG. 5B, may contain abrasive members comprising a thin band 505 attached to radial surface 506 and encircling ablation probe 504. As indicated by ablation probe 507, depicted in FIG. 5C, it also possible for the abrasive member to comprise small particle 508, conceptually similar to a grain of grit on a piece of sand paper, attached to the proximal surface 509 and/or radial surface 510 of ablation probe 507. It is also possible, as indicated by ablation probe 511, depicted in FIG. 5D, for the abrasive member to comprise a protrusion 512 extending from a surface of the ablation probe 511 other than proximal surface 513. It should be appreciated that the ablation probes depicted in FIG. 5 may be constructed by attaching or affixing the depicted abrasive members to their proximal and/or radial surfaces. Alternatively, the ablation probes depicted in FIG. 5 may be constructed such that the abrasive members are extensions of or integral with the ablation probes.

Figure 6:
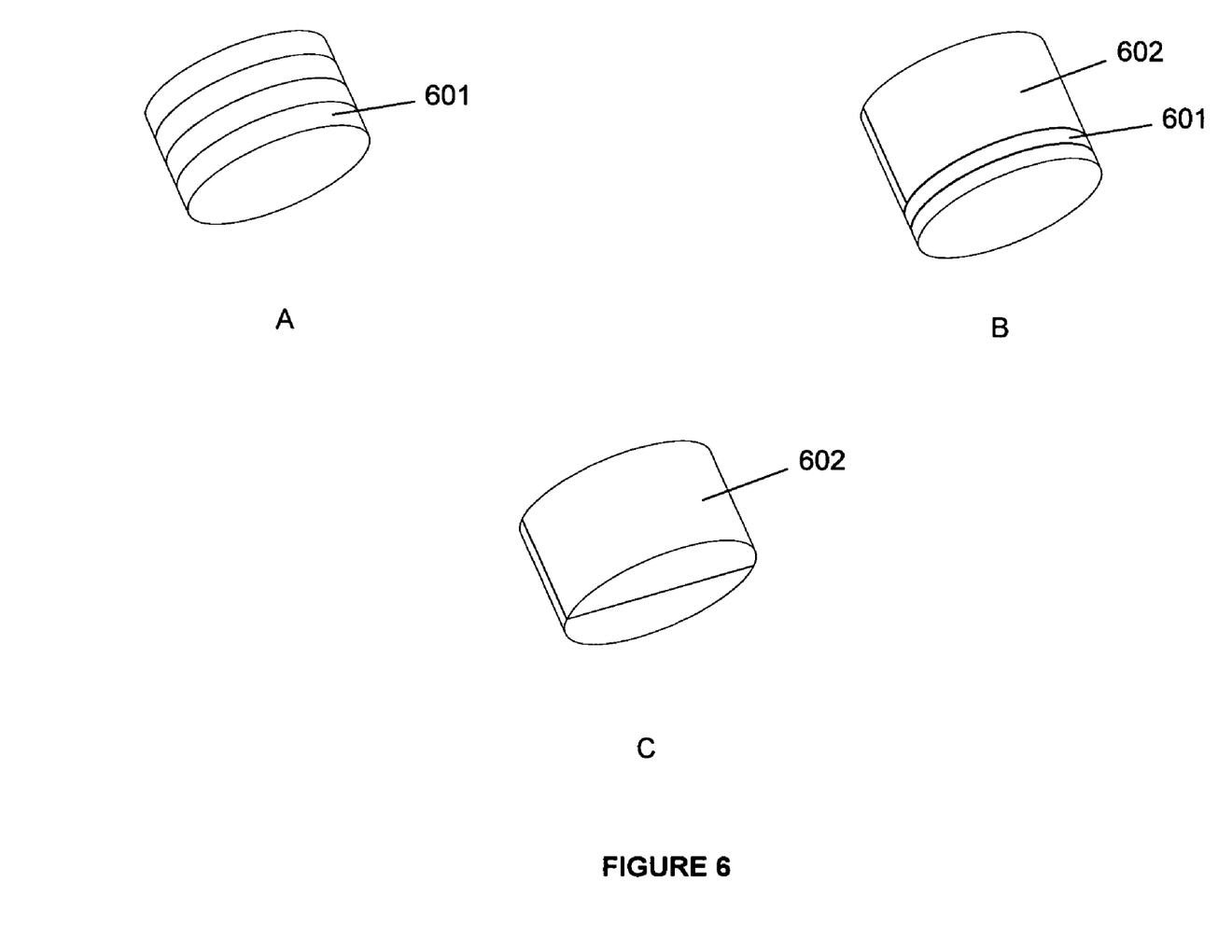
FIG. 6 depicts different piezo ceramic disc configurations that may be included within the transducer utilized to drive the ablation probe.

FIG. 6 depicts different piezo ceramic disc configurations that may be included within the transducer utilized to drive the ablation probe. The transducer may be comprised of a single piezo ceramic disc. Alternatively, the transducer may contain a collection of piezo ceramic discs as depicted in FIG. 6. For instance, the transducer may contain a collection cylindrical piezo ceramic discs 601 stacked upon one another in a manner resembling a roll of coins, as depicted in FIG. 6A. Such an arrangement may impart an axial or longitudinal displacement upon the driven ablation probe when the transducer is energized. Alternatively, the transducer may contain a pair of half cylindrical piezo ceramic discs 602 combined to form a cylinder, as depicted in FIG. 6C. Such an arrangement may impart a circumferential displacement upon the driven ablation probe when the transducer is energized. The transducer may also contain a combination of cylindrical piezo ceramic discs 601 and half cylindrical piezo ceramic discs 602, as depicted in FIG. 6B. Such a combination arrangement may impart an axial and circumferential displacement upon the driven ablation probe when the transducer is energized.

The ultrasound transducer responsible for driving the ablation probe need not be in direct contact with the ablation probe. Instead, the transducer may be in communication with the guide wire attached to the ablation probe, driving the ablation probe through said communication. In such an embodiment, the transducer may be located anywhere within the ablative apparatus, including, but not limited to, the handle. The transducer may also be located elsewhere within the ablative apparatus, provided the transducer is in direct or indirect communication with the ablation probe.

The transducer utilized in the ablative apparatus should be capable of inducing the ablation probe to vibrate at a frequency between approximately 20 kHz and approximately 20 MHz. The recommended frequency of vibration is approximately 30 kHz to approximately 40 kHz. The transducer should also be capable of driving the transducer with ultrasonic energy having an intensity of at least approximately 0.1 Watts per centimeter squared.

Pulse duration and treatment time are dependent upon the depth and type of lesion the surgeon wishes to induce. Pulsing the ultrasound energy driving the transducer by repeatedly turning the transducer on and off gives the surgeon control over lesion depth. Incorporating an ultrasound controller may permit the surgeon to control, regulate, or adjust, the pulse duration and pulse frequency of the driving ultrasound. Adjusting the pulse frequency and duration enables the surgeon to control the depth of the lesion inflicted by the ablation probe.

When the ablation probe has been advanced to the desired lesion location, the surgeon may retract the catheter as to expose the ablation probe's abrasive member(s). The surgeon may then mechanical induce an abrasion by driving the ablation probe with ultrasound energy generated by the transducer. Alternatively, the surgeon may not expose the ablation probe's abrasive members but rather activate the flow of cryogenic material through the ablative apparatus as to induce a lesion by means of cryoablation. If the surgeon wishes to induce a continuous lesion across a segment of cardiac tissue, the surgeon may activate the transducer as to prevent cryoadhesion of the catheter's distal end to the target tissue. Activating the transducer during cryoablation enables the surgeon to warm surface tissue at the site of ablation, thereby protecting surface tissue from ablation or injury. Likewise, activating the flow of cryogenic material through the apparatus while ultrasonically inducing a lesion enables the surgeon to cool surface tissue at the site of the ablation, thereby protecting it from ablation or injury.

Incorporating a mapping electrode placed at or near the distal end of the ablative apparatus may assist the surgeon in locating specific sites of arrhythmia. Alternatively, the mapping electrode may be located at or attached to the ablation probe. A mapping electrode may enable the surgeon to detect the electrical activity of the cells near the electrode. The surgeon could use the detected electrical activity to determine if the cells near the electrode are contributing to the arrhythmia. Furthermore, the surgeon may administer cryogenic energy to a region of myocardium suspected to be contributing to the patient's arrhythmia as to paralyze the tissue. If paralyzing the tissue completely or partially corrects the arrhythmia, the surgeon may then ablate the tissue with the ablation probe.

Incorporating a temperature sensor placed at or near the distal end of the ablative apparatus may enable the surgeon to monitor the temperature at the site of the ablation. Alternatively, the sensor may be located near or attached to the ablation probe. Monitoring the temperature near or at the site of the ablation with the temperature sensor may assist the surgeon in avoiding burning and/or inflicting other undesirable damage or injury. When the temperature of the tissue being ablated reaches or approaches an undesirable level, the surgeon could stop the ablation and allow the tissue to return to a safer temperature. The surgeon may also adjust the ultrasound parameters as to slow the change in temperature. If the ablative procedure being performed involves the administration of cryogenic energy, the surgeon may adjust the flow of the cryogenic material through the catheter system as to slow the change in temperature.

The ablative apparatus may also contain a drug lumen through which a drug solution or other fluid or composition may be introduced into the patient's body. Ultrasonically driving the ablation probe, while simultaneously delivering drug through the apparatus by way of the drug lumen, may be utilized by the surgeon to facilitate the release of the drug from the apparatus, as well as the penetration of the drug into targeted tissue.

The ablative apparatus may also contain a drug reservoir at its distal end. The drug reservoir may surround the ablation probe. Alternatively, the drug reservoir may be located distal to the ablation probe. When located distal to the ablation probe, the drug reservoir may contain slits at its base. The slits may completely or partially penetrate the base of the drug reservoir. Retracting the catheter may then cause the ablation probe to penetrate the base of the drug reservoir and eventually the distal end of the reservoir. Traveling through the drug reservoir, the ablation probe may be coated with a drug. Suspending the drug within a viscous or gel solution may offer better coating of the ablation probe as it travels through the drug reservoir. Ultrasonically driving the ablation probe will cause the drug solution clinging to the ablation probe to be liberated from the ablation probe and embedded in the tissue at and surrounding the site of the lesion. Similarly, ultrasonically driving the ablation probe while the probe is retracted may cause the release of drug from the drug reservoir.

Alternatively, drug delivery during the induction of lesions may be accomplished by first coating the ablation probe with a pharmacological compound. As in the above mention embodiment, ultrasonically driving the ablation probe will liberate the drug compound coating; dispersing it into the targeted tissue.

It should be appreciated that the term "cryoadhesion," as used herein, refers to the freezing of a cooled and/or cold object to tissues of the body.

It should be appreciated that the term "biologically compatible polymer," as used herein, refers to polymers, or plastics, that will not normally irritate or harm the body. Such polymers are familiar to those skilled in the art.

It should be appreciate that term "piezo ceramic disc," as used herein, refers to an element composed of a ceramic material that expands and contracts when exposed to an alternating voltage. Such ceramics are well known to those skilled in the art.

It should be appreciated that "energizing the transducer," as used herein, refers to inducing the contraction and expansion of piezo ceramic discs within the transducer by exposing the discs to an alternating voltage, as to induce the generation of ultrasonic energy.

It should be appreciated that the term "ultrasonically driven," as used herein, refers to causing the ablation probe to move by applying to the probe ultrasonic energy generated by a transducer in direct or indirect contract with the probe. The induced movement of the probe may include vibrating, oscillating, and/or other manners of motion.

It should be appreciated that the term "pulse duration," as used herein, refers to the length of time the transducer is generating ultrasonic energy.

It should be appreciated that the term "pulse frequency," as used herein, refers to how often the ultrasound transducer generates ultrasound during a period of time.

It should be appreciated that the term "mechanical ablation," as used herein, refers to injuring a tissue by scratching the tissue as to create an abrasion in the tissue.

It should be appreciated that the term "surgeon," as used herein, references all potential users of the disclosed ablative apparatus and does not limit the user of the apparatus to any particular healthcare or medical professional or healthcare or medical professionals in general.

It should be appreciated that elements described with singular articles such as "a", "an", and/or "the" and/or otherwise described singularly may be used in plurality. It should also be appreciated that elements described in plurality may be used singularly.

Although specific embodiments of apparatuses and methods have been illustrated and described herein, it will be appreciated by those of ordinary skill in the art that any arrangement, combination, and/or sequence of that is calculated to achieve the same purpose may be substituted for the specific embodiments shown. It is to be understood that the above description is intended to be illustrative and not restrictive. Combinations of the above embodiments and other embodiments as well as combinations and sequences of the above methods and other methods of use will be apparent to individuals possessing skill in the art upon review of the present disclosure.

The scope of the claimed apparatus and methods should be determined with reference to the appended claims, along with the full scope of equivalents to which such claims are entitled.

I claim:

1. An ablative apparatus comprising:
   a. An ablation probe containing:
      i. a proximal surface;
      ii. a distal surface opposite the proximal surface;
      iii. at least one radial surface extending between the proximal surface and the distal surface; and
      iv. at least one abrasive member on a surface of the ablation probe other than the proximal surface;
   b. A transducer capable of ultrasonically driving the ablation probe in contact with the proximal surface of the ablation probe containing:
      i. at least one piezo ceramic disc; and
      ii. electrodes capable of exposing the at least one piezo ceramic disc to an alternating voltage;
   c. A guide wire secured at one end to the transducer;
   d. A handle secured at the end of the guide wire opposite the transducer;
   e. Electrical leads running along the guide wire and connected to electrodes within the transducer;
   f. A catheter encasing the ablation probe, transducer, and at least a portion of the guide wire containing:
      i. a proximal end;
      ii. a distal end opposite the proximal end;
      iii. a pocket at the distal end of the catheter encasing the ablation probe;
      iv. a cryogenic intake lumen originating at the proximal end of the catheter and running substantially the length of the catheter;
      v. a cryogenic exhaust lumen running substantially the length of the catheter, substantially parallel to the cryogenic intake lumen, and terminating at the proximal end of the catheter;
      vi. a junction connecting the intake lumen and exhaust lumen at distal ends of the intake and exhaust lumens; and
      vii. a partition distal to the junction isolating the intake lumen and exhaust lumen from the pocket encasing the ablation probe.

2. The apparatus according to claim 1 further characterized by the catheter being composed of a biologically compatible polymer.

3. The apparatus according to claim 1 further comprising a sealed tip at the distal end of the pocket encasing the ablation probe containing one or a plurality of slits at least partially penetrating the sealed tip.

4. The apparatus according to claim 1 further characterized by the transducer containing a stack of piezo ceramic discs.

5. The apparatus according to claim 1 further characterized by the transducer containing at least one pair of half cylindrical piezo ceramic discs combined to form a cylinder.

6. The apparatus according to claim 1 further characterized by the at least one abrasive member on the ablation probe comprising a protrusion extending from a surface of the ablation probe other than its proximal surface.

7. The apparatus according to claim 1 further characterized by the at least one abrasive member on the ablation probe comprising a thin band on a radial surface of the ablation probe spiraling around the ablation probe.

8. The apparatus according to claim 1 further characterized by the at least one abrasive member on the ablation probe comprising a thin band on a radial surface of the ablation probe encircling the ablation probe.

9. The apparatus according to claim 1 further characterized by the at least one abrasive member on the ablation probe comprising a small particle on a surface of the ablation probe other than its proximal surface.

10. The apparatus according to claim 1 further characterized by the junction connecting the intake lumen and exhaust lumen of the catheter comprising at least one port connecting the intake and exhaust lumens.

11. The apparatus according to claim 1 further comprising a cryogenic storage unit in fluid communication with the cryogenic intake lumen via cryogenic feed tubing attached to a proximal end of the intake lumen.

12. The apparatus according to claim 1 further comprising a cryogenic retrieval unit in fluid communication with the cryogenic exhaust lumen via cryogenic exhaust tubing attached to a proximal end of the exhaust lumen.

13. The apparatus according to claim 1 further characterized by the transducer being capable of inducing the ablation probe to vibrate at a frequency between approximately 20 khz and approximately 20 mhz.

* * * * *